United States Patent [19]

Goldberg

[11] Patent Number: 4,614,721
[45] Date of Patent: Sep. 30, 1986

[54] HEAT RECOVERY CALORIMETER

[75] Inventor: Ira B. Goldberg, Thousand Oaks, Calif.

[73] Assignee: Rocwell, El Segundo, Calif.

[21] Appl. No.: 680,193

[22] Filed: Dec. 10, 1984

[51] Int. Cl.⁴ .......................................... G01N 25/30
[52] U.S. Cl. ................................... 436/147; 374/37; 374/38; 422/51; 422/94; 422/95; 436/159
[58] Field of Search .......................... 422/51, 94, 95; 436/147, 159; 374/31, 36, 37, 38

[56] References Cited

U.S. PATENT DOCUMENTS 3,589,184  6/1971  Moore .
3,783,684  1/1974  De Livois .
4,329,873  5/1982  Maeda .
4,329,874  5/1982  Maeda .
4,337,654  7/1982  Austin .
4,384,792  5/1983  Sommers et al. ...................... 374/36

Primary Examiner—Frank Sever
Attorney, Agent, or Firm—H. Fredrick Hamann; Craig O. Malin; John J. Deinken

[57] ABSTRACT

A catalytic calorimeter measures the heat value of a gas and includes a chamber for receiving gas and air. A catalyst within the chamber causes the combustion of the gas and air, while a first thermocouple provides a signal indicating the temperature of the gas and air prior to combustion. A second thermocouple indicates the temperature of the catalyst, which is heated by an electrical resistance heater. A first temperature controller is connected to the second thermocouple and the heater for maintaining the catalyst at a predetermined temperature. A heat sink within the chamber absorbs heat from the products of the combustion of the gas and a third thermocouple indicates the temperature of the heat sink. A Peltier effect thermoelectric cooler is provided to remove heat from the heat sink. A second temperature controller connected to the third thermocouple and the cooler maintains the heat sink at a predetermined temperature. An output device records the amount of heat supplied to the catalyst and the amount of heat removed from the heat sink.

11 Claims, 1 Drawing Figure

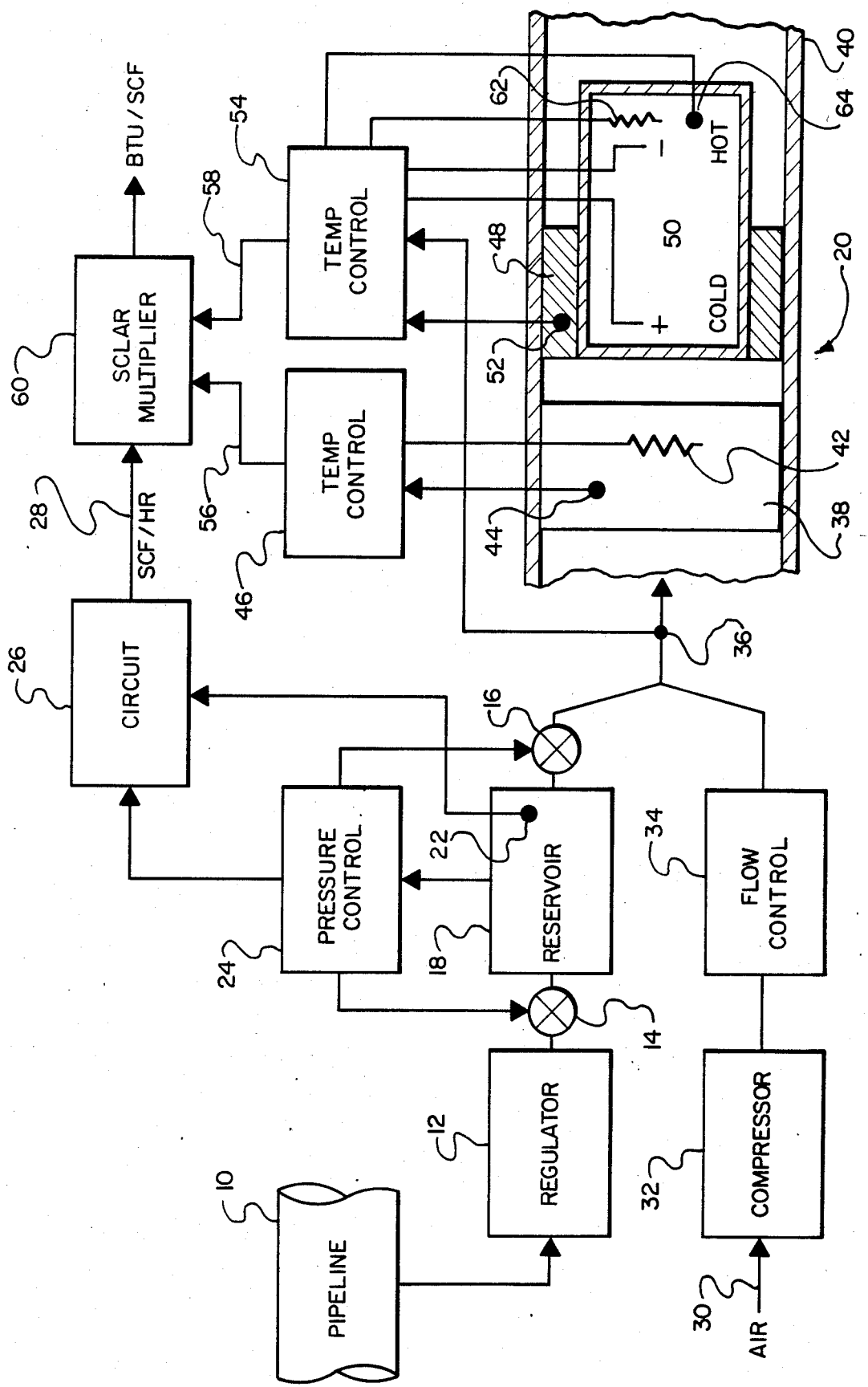

HEAT RECOVERY CALORIMETER

BACKGROUND OF THE INVENTION

This invention relates to calorimeters for measuring the heating values of gaseous fuels.

Prior to the 1970s, the cost of pipeline gas and the heat value (BTU content) were more or less constant. Infrequent measurements of BTU content were accomplished by flame calorimeters, while less elaborate and less expensive calorimeters were used for non-critical determinations. With the advent of energy shortages in recent years, there has been a large increase in the cost of natural fuels, as well as a general decrease in the quality of the fuels available. The BTU content of the fuels became more important as suppliers began to mix alternate source gases containing various compositions. As a result, natural gas fuel is now subject to a large variability in heat value and, because of the increased cost, it is becoming more important to charge customers according to the amount of energy which is consumed, rather than solely by the volume of gas which is used.

There are six main methods which have been used to determine the heat value of gaseous fuels: combustion calorimetry, gas chromatography, absorption spectrometry, oxygen titration/flame temperature measurement, mass spectrometry, and gas density.

The standard method used to measure the energy content of natural gas is low temperature combustion calorimetry, in which the gas is burned and the heat produced is transferred to a thermal reservoir, so that the temperature of the product gases rises only a few degrees above the initial temperature. This temperature rise can be measured accurately (to better than 0.001°) and is directly proportional to the energy content of the gas, so that the BTU value of the gas may be readily determined from the temperature increase.

The combustion reaction is typically accomplished at 60° F. so that the reference states of the products are gaseous $CO_2$ and liquid $H_2O$. The advantage of this low temperature approach is that it yields standard states (ASTM conditions), with no systematic uncertainty. Since this method provides a direct measure of the energy content of the gases and the small temperature rise can be measured quite accurately, it is an extremely precise technique.

While low temperature calorimetry has been widely used, it has some inherent difficulties. Most such measurement systems require ambient temperature control or air conditioning, and flow measurements must be accurate. Furthermore, such instruments are generally too large to be used in field applications.

Other methods of calorimetry, such as high temperature calorimetry or catalytic combustion calorimetry, have been used to reduce the expense and increase the response time of the measurement. The combustion method may be accomplished more rapidly by burning the fuel gas in a diluent and measuring the temperature increase, a method known as high temperature or net value calorimetry. The reaction proceeds as in the low temperature approach, but the resulting product is gaseous $H_2O$. At higher temperatures, sufficient heat is consumed in raising the temperature of the product gases and vaporizing the water produced to create considerable uncertainty in the actual heat which is referred to standard conditions. A single calibration gas cannot be used effectively, since the amount of water produced varies with the composition of the gas.

Catalytic combustion, rather than direct combustion, can also be used to measure BTU content. In a catalytic measurement system, the gas/air mixture is passed over a catalyst, such as Ni or Pd, causing the oxygen in the mixture to oxidize the hydrocarbon. This reaction produces heat, but the catalyst acts as a heat sink. For continuous measurement, the gas is flowed through a porous catalyst, and an electronic control circuit supplies heat via a heater embedded in the catalyst to maintain the measurement cell at a temperature equal to a reference cell. This method is potentially relatively simple and inexpensive, and the fact that a temperature difference is maintained reduces the uncertainties created by changes in the ambient temperature, pressure, and humidity.

Although a variety of heat measurement techniques are available in the art, a need has developed, particularly with the increase in fuel costs and the decrease in consistency of natural fuel gases, for a measurement technique which is highly accurate without being overly expensive. The high temperature calorimetry techniques known in the art incorporate inherent uncertainties in heating inert gas components and product mixtures and in vaporizing the water produced by the combustion reaction. These uncertainties cannot be completely eliminated unless the composition of the mixture is known. Thus a need has developed for a portable calorimetric technique which can operate at high temperatures, can provide heat values at standard conditions, and is simple and reliable in both the mechanical and electronic aspects of its design.

SUMMARY OF THE INVENTION

An instrument for measuring the quantity of heat introduced into the combustion products of a gas includes a chamber for receiving the combustion products and a heat sink within the chamber for absorbing heat from the combustion products. A temperature sensor provides a signal indicating the temperature of the heat sink and a cooling device removes heat from the heat sink. A temperature controller connected to the temperature sensor and the cooling device maintains the heat sink at a predetermined temperature, while an output device connected to the temperature controller records the amount of heat removed from the heat sink.

In a more particular embodiment, the chamber is a heat insulated tube and the heat sink is porous so that the combustion products can flow therethrough. The instrument may further include a flow controller for measuring the quantity of the combustion products which passes through the heat sink as a function of time, in which case the output device is connected to the flow controller to record the quantity of the combustion products which passes through the heat sink as a function of time and is adapted to record the amount of heat removed from the heat sink as a function of time.

A catalytic calorimeter for measuring the heat value of a gas includes a chamber for receiving the gas and air, with a catalyst within the chamber for causing the combustion of the gas and air. A first temperature sensor provides a signal indicating the temperature of the gas and air prior to combustion and a second temperature sensor provides a signal indicating the temperature of the catalyst. A first temperature controller, in conjunction with the second temperature sensor and a heater, maintains the catalyst at a predetermined temperature.

A heat sink within the chamber absorbs heat from the products of the combustion of the gas, with a third temperature sensor indicating the temperature of the heat sink. A second temperature controller, in conjunction with the third temperature sensor and a cooling device, maintain the heat sink at a predetermined temperature. An output device records the amount of heat supplied to the catalyst and the amount of heat removed from the heat sink.

In a more particular embodiment, the catalyst and the heat sink are porous to allow the gas and combustion products to pass therethrough. The calorimeter may further include a flow controller for measuring the quantity of the gas which passes through the catalyst and the heat sink as a function of time. In the latter embodiment, the output device is also connected to the flow controller to record the quantity of the gas which passes through the heat sink as a function of time, is adapted to record the amount of heat supplied to the catalyst as a function of time, and is adapted to record the amount of heat removed from the heat sink as a function of time.

A method of measuring the quantity of heat introduced into the combustion products of a gas includes the steps of providing a chamber for receiving the combustion products and absorbing heat from the combustion products in a heat sink in the chamber. The temperature of the heat sink is sensed and sufficient heat is removed from the heat sink to maintain the heat sink at a predetermined temperature. The amount of heat removed from the heat sink is recorded.

A method of measuring the heat value of a gas includes the steps of receiving the gas and air in a chamber and measuring the temperature of the gas and air prior to combustion. The air and gas is contacted with a catalyst in the chamber to cause the combustion of the gas. The temperature of the catalyst is measured and the catalyst is heated to maintain it at a predetermined temperature. A heat sink in the chamber absorbs heat from the products of the combustion, with heat being removed from the heat sink to maintain it at a predetermined temperature. The amount of heat supplied to the catalyst and the amount of heat removed from the heat sink are recorded.

BRIEF DESCRIPTION OF THE DRAWINGS

Additional details of the invention are presented in the description below, which refers to the drawing, which is a schematic diagram of a heat recovery calorimeter measurement system using the present invention.

DESCRIPTION OF THE INVENTION

High temperature (net calorific value) calorimeters exhibit inherent uncertainties when used to monitor the heating value of a gaseous fuel. This invention provides an effective way to reduce these uncertainties by monitoring the heat used in raising the temperature of the product gases and inert components of the fuel.

The FIGURE is a schematic diagram illustrating a heat recovery calorimeter measurement system which utilizes the techniques of the present invention. In this system, high pressure gas from a pipeline 10 is routed through a pressure regulator 12, so that the calorimeter can operate at a pressure which allows the pipeline gas sample to be treated as an ideal gas. A pair of valves 14 and 16 are used to fill a reservoir 18 of known volume and to bleed the gas into a calorimeter 20 at a controlled rate. The temperature and pressure in the reservoir are measured by a thermocouple 22 and a pressure controller 24. The temperature and the time rate of change of pressure in the reservoir are monitored by a circuit 26 to determine the volume rate of flow of the gas through the calorimeter on the basis of ASTM conditions (a standard temperature of 60° F. and a standard pressure of 14.73 psi). The circuit 26 provides an output 28 indicating SCF/hour of the sample gas.

Input air 30, which is provided in a relatively large volume as compared to the gas volume, is used to supply oxygen for combustion of the gas. In order to reduce the residual water vapor pressure to less than 2% of the saturation value of the expanded gas, the air is dried in a compressor 32. The rate at which the dried air is supplied to the calorimeter is accurately measured and controlled by a mass flow meter-controller 34.

The temperature of the air and fuel gas mixture is measured before the mixture enters the calorimeter by a thermocouple 36. The mixture is then catalytically burned as it passes through a porous catalyst 38, which fills the cross sectional area of an insulated tube 40. The catalyst is maintained at a constant temperature by an electrical resistance heater 42 and a thermocouple 44 in conjunction with a temperature controller 46. The catalyst temperature is maintained slightly above what would be the steady state temperature with a high BTU gas flowing through the system. If the BTU content of the gas being measured is lower than that of the high BTU gas, the heater 42 is activated by the controller 46 to keep the steady state temperature of the catalyst at the constant temperature.

One of the primary differences among the various pipeline gases is the amount of water which is formed in the combustion products of those gases. Thus, to obtain an accurate heating value for the sampled gas, the power used to heat the catalyst must be corrected to a temperature at which most of the water produced by the combustion process condenses. It is an outstanding feature of this invention to provide an instrument in which this correction is made automatically, thereby providing significantly increased accuracy in the measurement of heat value. To accomplish the correction, the combustion products from the catalytic burner flow through a porous heat sink 48, which absorbs the heat acquired by the combustion products. The heat sink is in thermal contact with the cold end of a Peltier effect thermoelectric cooler 50. The temperature of the heat sink is measured by a thermocouple 52, the output of which is used by a second temperature controller 54 to determine the amount of heat removed from the heat sink by means of the cooler 50. The power which is consumed in reducing the temperature of the combustion products to the pre-combustion temperature (as measured by thermocouple 36) is related to the total heat content of the gas. There will be slightly different heat capacities for the $CO_2$ and $H_2O$ vapors. If the steady state temperature is approximately 300°–400° C., however, the variation due to the different products will be small.

The total energy per SCF will then be based on the SCF flow, as determined by the pressure, volume flow, and temperature of the gas; the energy used to keep the catalyst at a constant temperature; and the energy used to reduce the temperature of the combustion products. These quantities are supplied, via lines 28, 56, and 58, to a scalar multiplier 60, which provides an output for the heating value of the gas in BTU/SCF.

The theory of the calorimetric determination is based on low temperature combustion and heating a gas and recovering the heat from the gas. The catalytic portion of the calorimeter burns the gas sample with excess air at a fairly low temperature (<400° C.) in the presence of a catalyst. The catalyst does not change the heat generated by the reactions, which is given by:

$$C_nH_{2n+2}(g) + \qquad (1)$$
$$(\tfrac{1}{2})(3n+1)O_2(g) + 3.773(\tfrac{1}{2})(3n+1)N_2(g) + Xs\ Air \rightarrow$$
$$n\ CO_2(g) + (n+1)H_2O(g) + 3.773(\tfrac{1}{2})(3n+1)N_2(g) + Xs\ Air$$

In the absence of excess air, the ideal adiabatic flame temperature is about 3500° F. for methane. Excess air will cool the flame, however. As an example of how the first part of the calorimeter will operate, consider the case of methane combustion. The thermomechanical reaction which takes place at the elevated temperature is:

$$CH_4(g) + 2O_2(g) \rightarrow CO_2(g) + 2H_2O\ (g) \qquad (2)$$

because the water is in the form of gas. The heat of reaction for gaseous products, $\Delta H_{60}(g)$, after correction for the heat capacity of the gas, is given by:

$$-\Delta H_{60}(g) = -\Delta H_c^o + \Delta H_v \qquad (3)$$

where $\Delta H_c^o$ is the standard heat of combustion with the products and reactants saturated with $H_2O$, and $\Delta H_v$ is the heat of vaporization of the water produced. The standard heat of combustion of methane is 1011.99 BTU/SCF, while the heat loss due to vaporization of water would be 100.62 BTU/SCF. In this case, it makes little difference whether the air is moist or dry, and the total heat liberated in the reaction is 911.37 BTU/SCF. The final temperature of the mixture is then equivalent to burning the gas at room temperature and heating the reactants such that 911.37 BTU/SCF is consumed. For simplicity in this calculation, the average heat capacity of a gas, $\overline{C}_p(j)$, over the initial to final temperatures can be defined as:

$$\overline{C}_p(j) = [1/(T_F - T_I)] \cdot \int_{T_I}^{T_F} C_p(j) dT \qquad (4)$$

Equation (4) treats the heat capacity as a constant. This is not exactly valid over large temperature ranges as shown, so Equation (4) must be corrected for the heat capacity of the gas at different temperatures. Using this method, the final temperature of the gas burned with excess air can be determined by:

$$T_F = [-\Delta H_c(g)]/[\Sigma_j n_j \overline{C}_p(j)] + T_I \qquad (5)$$

where $n_j$ is the number of moles of each gas, including unconsumed air. At ASTM conditions, 1 SCF contains 1.198 moles of gas. As a result, for methane combustion, the products contain 7.546 moles of $N_2$, 1.198 moles of $CO_2$, and 2.396 moles of $H_2O$, as well as whatever excess air was used. To reach a 400° C. temperature, about 61 SCF of excess air must be added to 1 SCF of methane. When this gas mixture is cooled at 60° F., all of the heat, including the heat of vaporization, must be removed. It is clear, therefore, that the heat determined from the catalytic burner is smaller than the thermoelectric cooler.

One advantage of the calorimeter of this invention is that the operating conditions can be set for optimum performance. Once the temperature of the catalyst is established, the relative flow rates of gas and air can be determined so that minimum electrical heating of the catalyst is needed for the anticipated maximum BTU content. Furthermore, the system can be calibrated for the maximum BTU gas by relating this gas composition to methane. During calibration, the catalyst heater current, air flow rate, and gas flow rate can be adjusted. The equation which governs the air flow rate, $v_A$, based on the final temperature is:

$$v_A = v_G[-\Delta H_c^o - n_w\Delta H_v - (\Sigma_j n_j \overline{C}_p(j))(T_F - T_I)]/(\overline{C}_p\ (air)) \qquad (6)$$

where $v_A$ is the pipeline gas flow rate and $\Delta H_v$ and $\overline{C}_p(j)$ are given in terms of SCF, and $n_w$ is the amount of water produced in the combustion reaction. If a gas with a smaller BTU content is measured, an amount of current will heat the catalyst, such that:

$$I^2R/3.413 = [-\Delta H_c^o(s) + \Delta H_c^o(g)] \qquad (7)$$
$$- [n_w(s) - n_w(g)]\Delta H_v$$
$$- (T_F - T_I)\Sigma_j[n_j(s) - n_j(g)]\overline{C}_p(j)$$

where I is current (amperes), R is resistance (ohms), and the parentheticals s and g represent the standard reference point reaction and the reaction of the gas, respectively. Often the $n_j$'s are not known since the gas composition is not known. The terms in Equation (7) are arranged in order of likely importance based on low temperature calorimetry. Most likely, the catalytic unit itself will be accurate to 10-20 BTU/SCF, since differences between $n_j(s)$ and $n_j(g)$ are frequently small. It is therefore clear that the heat of water vaporization must be recovered. If dry air is used in the calorimeter instead of moist air, then the correction may be applied to the BTU content to saturate the air.

In order to recover the heat generated, the gas must be cooled to the initial temperature. Assuming the conditions described following Equation (5), the heat content of the gas:

$$\Delta H = \Sigma_j \overline{C}_p(j)\Delta T \qquad (8)$$

can be about 1.26 BTU/SCF.

One method of recovering the heat from the gas is to cool the gas via a thermoelectric refrigerator, such as a Peltier effect device. The Peltier effect device works because current across a junction of two dissimilar conductors causes a temperature gradient. If a complete circuit is constructed, then heat is removed from one junction and added to the second junction where the power supply is connected. The thermoelectric refrigerator is used such that the cold end cools the gas and the warm end liberates excess heat. The coefficient of performance, C, defined as the cooling output/power input, is given by:

$$C = [S_{12}I_pT_2 - I_p^2R_T/2 - K_T(T_1 - T_2)]/[S_{12}I(T_1 - T_2) + I^2R_T] \qquad (9)$$

where $S_{12}$ is the Seebeck coefficient of the conducting pair, $I_p$ is the current through the device, $R_T$ is the resistance of the conductors, and $K_T$ is the thermal conductivity multiplied by the area and divided by the length of the conductor for an ideal source.

Equation (9) shows that at the maximum temperature difference, no cooling takes place. In this case, the performance coefficient C is 0 and:

$$T_1-T_2=Z_{12}T_2^2/2 \qquad (10)$$

where the figure of merit $Z_{12}$ is given by:

$$Z_{12}=S_{12}^2/[(k_1p_1)^{\frac{1}{2}}+(k_2p_2)^{\frac{1}{2}}]^2 \qquad (11)$$

where $k_i$ is the thermal conductivity and p is the resistivity of the thermoelectric elements. Typically $Z_{12}$ ranges between $10^{-5}$ and $10^{-2}$. Maximum temperature differences of 100° C. for single element devices have been obtained with n-type and p-type bismuth telluride. Maximum cooling (maximum C) occurs when:

$$I=S_{12}(T_1-T_2)/R_T[(1+Z_{12}(T_1+T_2)/2)^{\frac{1}{2}}-1] \qquad (12)$$

and $$C=T_2(T_1-T_2)^{-1}[(1+(\tfrac{1}{2})Z_{12}(T_1+T_2))^{\frac{1}{2}}-T_1/T_2]\cdot[(-1+(\tfrac{1}{2})Z_{12}(T_1-T_2))^{\frac{1}{2}}+1]^{-1} \qquad (13)$$

Thus the smaller the difference between $T_1$ and $T_2$, the greater the cooling efficiency. As a consequence of these relationships, the temperature of the heat dissipation end of the thermoelectric cooler must be carefully controlled. A large T will provide high precision, but low efficiency. Furthermore, the operating conditions must be calibrated. Not all of the parameters are known with sufficient accuracy to monitor the BTU content. In operation, the temperature of the hot end of the thermoelectric cooler can be controlled, if necessary, by an auxiliary heater, such as the electrical resistance heater 62 shown in FIG. 1. The cooling efficiency is strongly dependent on the temperature difference between the junctions, so that temperature stability of the thermoelectric device is critical in order to maintain a linear relationship between the power input and heat removal. This temperature difference is monitored by the controller 54 in conjunction with the thermocouple 52 and a thermocouple 64 located at the hot end of the cooler 50. The operating conditions must be selected to maintain a balance between cooling effectiveness and the variation with temperature. A practical unit for this application should have a cooling capacity of 100–200 BTU/hr.

In the absence of heat loss from the calorimeter, two heat outputs are obtained. The Peltier device must be calibrated, but after calibration of the current $I_p$ to the thermal content of the gas $\Delta \dot{H}_p$ is given by:

$$\Delta \dot{H}_p(I_p)=-\Delta \dot{H}_c+I^2R/3.413+\Delta \dot{H}_s \qquad (14)$$

where $\Delta \dot{H}_s$ is the amount of heat in BTU/hr required to saturate the dry air and gas which is fed into the calorimeter. The BTU content required to saturate the vapor is 0.6–3.6 BTU/SCF of total gas, depending on the initial gas temperature between 50° and 90° F. The latter term can be important at large gas volumes.

Calibration of the Peltier device can be accomplished by a standard gas such as methane, or by passing a known current through a catalyst heater while burning a known volume of gas.

This device will provide a continuous value, and the resulting heat of combustion will be equivalent to the heating value at standard temperature and pressure. The accuracy of the instrument is determined by the precision of the flow controllers and the temperature stability which can be maintained at the catalyst and the heat sink. Among the major advantages of this technique are that the BTU content of the fuel is measured essentially at standard conditions. All gaseous water is condensed to the liquid state, and all heated gases are cooled to ambient. As a result, the heat of vaporization of water and the heat required to raise the gas temperature is recovered. A further consequence is that inert components of the fuel, such as $N_2$ and $CO_2$, do not affect the accuracy of the measurement. The unit will also be essentially maintenance free. Combustion can be carried out in air, so that no chemical supply for the device is required. Since the combustion is catalytic, oxidation of the fuel is carried out at much lower temperatures than in other calorimeters, so that the reliability of the unit is very good. As in all units, calibrations must be performed periodically, so that some gas supply is necessary.

A significant advantage of this unit is the extreme simplicity of the electronic control circuitry which is required. No integrating or major programming steps, such as are used in gas chromatography and infrared spectroscopy, are required. The BTU value is simply equal to the sum of the catalyst heater and thermoelectric cooler currents, each multiplied by a calibration factor.

Another benefit of this design is the mechanical integrity of the device. Mechanical integrity is very high because the gas flows through the sensing elements, each of which fills an entire pipe section. Thus vibration should have little or no effect on the performance of this device in comparison to other calorimeter designs.

It will be important to avoid damage to the catalyst by poisoning, thermal degradation, or plugging by residue buildup. Furthermore, the linearity of the thermoelectric cooling process may be distorted if high cooling rates are required.

A preferred embodiment of the invention has been illustrated and discussed above. Modifications and additional embodiments, however, will undoubtedly be apparent to those skilled in the art. The illustrated embodiment, for example, uses compressed air to ensure that the air is dry. The incoming air could alternatively be saturated with water, an approach which is easier to implement but requires more maintenance and a reliable supply of clean water. Furthermore, equivalent elements may be substituted for those illustrated and described herein, parts or connections might be reversed or otherwise interchanged, and certain features of the invention may be utilized independently of other features. Consequently, the examples presented herein are not all inclusive, but are intended to teach those skilled in the art how to make and use the invention to advantage, while the appended claims are more indicative of the full scope of the invention.

I claim:

1. A method of measuring the heat value of a known quantity of a gas, comprising the steps of:
   receiving the gas and air in a chamber;
   measuring the temperature of the gas and air prior to combustion;
   contacting the gas and air with a catalyst filling the cross-sectionaly area of the chamber to cause the combustion of the gas;
   measuring the temperature of the catalyst;

heating the catalyst to maintain the catalyst at a predetermined temperature;

recording the amount of heat supplied to the catalyst;

absorbing heat from the products of the combustion in a heat sink in the chamber;

measuring the temperature of the heat sink;

removing heat from the heat sink to maintain the heat sink at a predetermined temperature;

recording the amount of heat removed from the heat sink; and manipulating means and thereby calculating the amount of heat produced by the quantity of gas by multiplying the heat supplied to the catalyst by a first calibration factor, multiplying the heat removed from the heat sink by a second calibration factor, and summing the two calibrated heat values.

2. The method of claim 1, wherein the catalyst further comprises a porous catalyst adapted for the gas to flow therethrough.

3. The method of claim 2, wherein the heat sink further comprises a porous heat sink adapted for the combustion products to flow therethrough.

4. The method of claim 3, further comprising the step of:

measuring the quantity of the gas which passes through the catalyst and the heat sink as a fuction of time; and wherein:

the step of recording the amount of heat supplied to the catalyst further comprises recording the amount of heat supplied to the catalyst as a function of time; and the step of recording the amount of heat removed from the heat sink further comprises recording the amount of heat removed from the heat sink as a function of time.

5. A catalytic calorimeter for measuring the heat value of a known quantity of a gas, comprising:

a chamber for receiving the gas and air;

a catalyst within the chamber and filling the cross-sectional area of the chamber for causing the combustion of the gas and air;

a first temperature sensor for providing a signal indicating the temperature of the gas and air prior to combustion;

a second temperature sensor for providing a signal indicating the temperature of the catalyst;

a heater for heating the catalyst;

a first temperature controller connected to the second temperature sensor and the heater for maintaining the catalyst at a predetermined temperature;

a heat sink within the chamber and filling the cross-sectional area of the chamber for absorbing heat from the products of the combustion of the gas;

a third temperature sensor for providing a signal indicating the temperature of the heat sink;

a cooling device for removing heat from the heat sink;

a second temperature controller connected to the third temperature sensor and the cooling device for maintaining the heat sink at a predetermined temperature; and an output device for receiving as inputs the quantity of the gas, the amount of heat supplied to the catalyst, and the amount of heat removed from the heat sink and calculating the amount of heat produced by the quantity of gas by multiplying the heat supplied to the catalyst by a first calibration factor, multiplying the heat removed from the heat sink by a second calibration factor, and summing the two calibrated heat values.

6. The instrument of claim 5, wherein the chamber further comprises a heat insulated tube.

7. The instrument of claim 6, wherein the catalyst further comprises a porous catalyst adapted for the gas to flow therethrough.

8. The instrument of claim 7, wherein the heat sink further comprises a porous heat sink adapted for the combustion products to flow therethrough.

9. The instrument of claim 8, further comprising:

a flow controller for measuring the quantity of the gas which passes through the catalyst and the heat sink as a function of time; and wherein the output device is further connected to the flow controller to record the quantity of the gas which passes through the heat sink as a function of time, is adapted to record the amount of heat supplied to the catalyst as a function of time, and is adapted to record the amount of heat removed from the heat sink as a function of time.

10. The instrument of claim 5, wherein:

the first, second, and third temperature sensors further comprise first, second, and third theremocouples;

the heater further comprises an electrical resistance heater;

the cooling device further comprises a Peltier effect thermoelectric device; and the first and second temperature controllers further comprise first and second electrical temperature control circuits.

11. The instrument of claim 10, wherein the output device further comprises an electrical circuit for recording the current applied to the heater as a function of time and recording the current applied to the thermoelectric device as a function of time.

* * * * *